United States Patent [19]
Coutos-Thevenot et al.

[11] Patent Number: 5,914,270
[45] Date of Patent: *Jun. 22, 1999

[54] METHOD FOR PROMOTING THE DIFFERENTIATION OF PLANT CELLS IN CULTURE

[75] Inventors: Pierre Marie Louis Coutos-Thevenot, Paris; Thierry Georges Jouenne, Rouen, both of France; Olivier Charles Antoine Maes, Sept-Iles, Canada; Alain Jean Deloire, Reims, France; Michel Paul Henri Boulay, Livry-sur-Seine, France; Jean René Denis Guern, Gif-sur-Yvette, France

[73] Assignee: LVMH Recherche, Nanterre, France

[*] Notice: This patent issued on a continued prosecution application filed under 37 CFR 1.53(d), and is subject to the twenty year patent term provisions of 35 U.S.C. 154(a)(2).

[21] Appl. No.: 08/448,481
[22] PCT Filed: Dec. 14, 1993
[86] PCT No.: PCT/FR93/01239
  § 371 Date: Aug. 8, 1995
  § 102(e) Date: Aug. 8, 1995
[87] PCT Pub. No.: WO94/13787
  PCT Pub. Date: Jun. 23, 1994

[30] Foreign Application Priority Data

Dec. 14, 1992 [FR] France .................................. 92 15044

[51] Int. Cl.⁶ .............................. C12N 5/00; C12N 5/02
[52] U.S. Cl. ........................ 435/430; 435/410; 435/420; 435/421; 435/430; 435/430.1; 435/431
[58] Field of Search ........................... 435/240.45, 240.4, 435/410, 420, 421, 430, 430.1, 431

[56] References Cited

U.S. PATENT DOCUMENTS 4,532,733  8/1985  Krul .
4,714,679  12/1987  Krul .

FOREIGN PATENT DOCUMENTS 0455597  11/1991  European Pat. Off. .
2537157  6/1984  France .
92 20801  11/1992  WIPO .

OTHER PUBLICATIONS

P. Coutos–Thevenot et al. Extracellular Protein Patterns Of Grapevine Cell Suspensions In Embryogenic And Non–Embryogenic Situations, Plant Science, vol. 86, No. 2, 1992, Limerick, Ie pp. 137–145.

P. Strek et al., Cell–Specific Expression Of The Carrot EP2 Lipid Transfer Protein Gene, The Plant Cell, vol. 3, No. 9, Sep. 1991, pp. 907–921.

M Grosbois et al., Changes In Level And Activity Of Phospholipid Transfer Protein During Maturation and Germination Of Maize Seeds, Plant Physiology, vol. 90, No. 4, Apr. 1989, pp. 1560–1564.

L. Sossountzov et al., Spatial And Temporal Expression Of A Maize Lipid Transfer Protein Gene, The Plant Cell, vol. 3, No. 9, Sep. 1991, pp. 923–933.

S. Torres–Schumann et al., A Probable Lipid Transfer Protein Gene Is Induced By NaCL In Stems Of Tomato Plants, Plant Molecular Biology, vol. 18, No. 4, Feb. 1992, pp. 749–757.

P. Coustos–Thevenot et al., Somatic Embryogenesis From Grapevine Cells. I–Improvement Of Embryo Development By Changes In Culture Conditions, Plant Cell Tissue And Organ Culture, vol. 29, No. 2, 1992, pp. 125–133.

P. Coutos–Thevenot et al., Four 9–kDa Proteins Excreted By Somatic Embryos Of Grapevine Are Isoforms Of Lipid–Transfer Proteins, European Journal Of Biochemistry, vol. 217, No. 3, Nov. 1993, pp. 885–889.

*Primary Examiner*—Leon B. Lankford, Jr.
*Attorney, Agent, or Firm*—Pollock, Vande Sande & Amernick

[57] ABSTRACT

A method for promoting differentiation of cells in culture. At least one lipid transfer protein or lipid transfer protein analog is introduced into a culture medium at a concentration that is effective for obtaining differentiation of cells in the culture medium. The lipid transfer protein or lipid transfer protein analog includes at least one amino acid sequence having at least 80% homology with a sequence depicted in FIG. 2.

29 Claims, 5 Drawing Sheets

|    | 1 |   |   |   | 5 |   |   |   |   | 10 |   |   |   |   | 15 |   |   |   |   | 20 |
|----|---|---|---|---|---|---|---|---|---|----|---|---|---|---|----|---|---|---|---|----|
| P1 | Ala | Ile | Thr | Cys | Gly | Gln | Val | Ser | Ala | Leu | Ser | Cys | Leu | Gly | Tyr | Leu | Lys | Asn |
| P2 | Ala | Ile | Thr | Cys | Gly | Gln | Val | Ser | Ala | Leu | Ser | Cys | Leu | Gly | Tyr | Leu | Lys | Asn |
| P3 | —  | Leu | Ser | Cys | Gly | Asp | Val | Ala | Thr | Gln | Met | Ala | Ser | Ile | Asn | Tyr | Leu | Arg | Gly |
| P4 | Thr | Val | Thr | Cys | Gly | Gln | Val | Ala | Ser | Ala | Leu | Ser | Pro | Cys | Ile | Asp | Tyr | Leu | Gln | Lys |

|    | 21 |   |   |   | 25 |   |   |   |   | 30 |   |   |   |   | 35 |   |   |   |   | 40 |
|----|----|---|---|---|----|---|---|---|---|----|---|---|---|---|----|---|---|---|---|----|
| P1 | Gly | Gly | Ala | Val | Pro | Pro | Gly | — | Ser | Ser | — | Cys | Gly | Ile | Lys | Asn | Leu | Asn | Ser | Ala |
| P2 | Gly | Gly | Ala | Val | Pro | Pro | Gly | — | Ser | Ser | — | Cys | Gly | Ile | Lys | Asn | Leu | Asn | Ser | Ala |
| P3 | Gly | Gly | Pro | Leu | Pro | Ala | Ala | — | — | — | Cys | Asn | Gly | Val | Lys | Ile | Leu | Lys | Leu | Ser |
| P4 | Asp | Gly | Ala | Val | Pro | Gly | Gly | — | Ser | Cys | — | Cys | — | X | Lys | X | Leu | Ser | Ser | Ala |

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| P1 | Ala | Ile | Thr | Cys | Gly | Gln | Val | Ser | Ala | Leu | Ser | Ser | Cys | Ser | Leu | Gly | Tyr | Leu | Lys | Asn |
| P2 | Ala | Ile | Thr | Cys | Gly | Gln | Val | Ser | Ala | Leu | Ser | Ser | Cys | Ser | Leu | Gly | Tyr | Leu | Lys | Asn |
| P3 | – | Leu | Ser | Cys | Gly | Asp | Val | Ala | Thr | Gln | Met | Thr | Cys | Ser | Ile | Asn | Tyr | Leu | Arg | Gly |
| P4 | Thr | Val | Thr | Cys | Gly | Gln | Val | Ala | Ser | Ala | Leu | Ser | Cys | Pro | Ile | Asp | Tyr | Leu | Gln | Lys |
| CARROT | Val | Leu | Thr | Cys | Gly | Gln | Val | Ser | Gly | Ala | Leu | Ala | Cys | Pro | Leu | Gly | Tyr | Leu | Arg | Ser |
| SPINACH | Gly | Ile | Thr | Cys | Gly | Gln | Val | Ser | Ser | Ala | Ile | Ala | Cys | Pro | Ile | Gly | Tyr | Leu | Lys | – |
| MILLET | Ala | Ile | Ser | Cys | Gly | Gln | Val | Ser | Ser | Ala | Ile | Ala | Cys | Pro | Leu | Ala | Tyr | Ala | Arg | Gly |
| CORN | Ala | Ile | Ser | Cys | Gly | Gln | Val | Ala | Ser | Ala | Ile | Gly | Cys | Pro | Ile | Ser | Tyr | Ala | Arg | Gly |
| BARLEY | Ala | Leu | Asn | Cys | Gly | Gln | Val | Asp | Ser | Lys | Met | Lys | Cys | Pro | Leu | Thr | Tyr | Val | Gln | Gly |
| RAPE | Ala | Val | Pro | Cys | Val | Thr | Val | Asp | Met | Ala | Ala | Lys | Ala | Ala | Val | Gly | F | Ala | Thr | Gly |

|  | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| P1 | Gly | Gly | Ala | Val | Pro | Pro | – | – | Ser | Ser | Gly | Ile | Asn | Leu | Lys | Leu | Asn | Ser | Ser | Ala |
| P2 | Gly | Gly | Ala | Val | Pro | Pro | – | – | Ser | Ser | Gly | Ile | Asn | Leu | Lys | Leu | Asn | Asn | Leu | Ala |
| P3 | Ala | Gly | Pro | Leu | Pro | Ala | – | Asn | – | Cys | – | Val | Ile | Lys | Val | Leu | Lys | Ser | Ala | Ser |
| P4 | Asp | Gly | Ala | Val | Pro | Ala | – | – | Asn | Cys | Val | X | X | Leu | X | Leu | Ser | Asn | Ser | Ala |
| CARROT | Gln | Gly | Asn | Val | Pro | Gly | Leu | Ser | Gly | Cys | Gly | Val | Gly | Leu | Val | Leu | Asn | Ala | Ala | Ala |
| SPINACH | Gly | Gly | Pro | Val | Gly | Gly | – | – | Ser | Cys | Asp | Gly | Val | Leu | Arg | Leu | Asn | Asn | Ala | Ala |
| MILLET | Gly | Gly | Ala | Leu | Pro | Ala | – | – | Gly | Gln | Ser | Gly | Ala | Leu | Lys | Leu | Ala | Ala | Ala | Ala |
| CORN | Gly | Gly | Ser | Ala | Pro | Ser | – | – | Ser | Gly | Ala | Gly | Ser | Leu | Arg | Leu | Asn | Ala | Ala | Ala |
| BARLEY | Gln | Pro | Pro | Gly | Pro | Ser | – | – | Asn | Glu | Cys | Gln | Cys | Leu | Arg | Leu | Asn | His | Asn | Ala |
| RAPE | Lys | Asp | Ser | Lys | Pro | Gln | – | – | Thr | Ala | Leu | Leu | Gln | Leu | Gln | Leu | – | – | Ala | Gln |

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 38 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:1:

Ala Ile Thr Cys Gly Gln Val Ser Ser Ala Leu Ser Ser Cys Leu Gly
1               5                   10                  15

Tyr Leu Lys Asn Gly Gly Ala Val Pro Pro Gly Ser Ser Cys Gly Ile
            20                  25                  30

Lys Asn Leu Asn Ser Ala
        35

(2) INFORMATION FOR SEQ ID NO:2:

(i) SEQUENCE CHARACTERISTICS:
       (A) LENGTH: 37 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:2:

Leu Ser Cys Gly Asp Val Ala Thr Gln Met Ala Ser Cys Ile Asn Tyr
1               5                   10                  15

Leu Arg Gly Ala Gly Pro Leu Pro Ala Ala Cys Cys Asn Gly Val Lys
            20                  25                  30

Ile Leu Lys Leu Ser
        35

(2) INFORMATION FOR SEQ ID NO:3:

(i) SEQUENCE CHARACTERISTICS:
       (A) LENGTH: 37 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:3:

Thr Val Thr Cys Gly Gln Val Ala Ser Ala Leu Ser Pro Cys Ile Asn
1               5                   10                  15

Thr Leu Gln Lys Asp Gly Ala Val Pro Ala Gly Ser Cys Cys Xaa Lys
            20                  25                  30

Xaa Leu Ser Ser Ala
        35

(2) INFORMATION FOR SEQ ID NO:4:

(i) SEQUENCE CHARACTERISTICS:
       (A) LENGTH: 40 amino acids
       (B) TYPE: amino acid
       (C) STRANDEDNESS: single (D) TOPOLOGY: unknown (ii) MOLECULE TYPE: peptide (xi) SEQUENCE DESCRIPTION: SEQ ID NO:4:

Val Leu Thr Cys Gly Gln Val Thr Gly Ala Leu Ala Pro Cys Leu Gly
 1               5                  10                  15

Tyr Leu Arg Ser Gln Val Asn Val Pro Val Pro Leu Thr Cys Cys Asn
                20                  25                  30

Val Val Arg Gly Leu Asn Asn Ala
            35                  40

(2) INFORMATION FOR SEQ ID NO:5:

(i) SEQUENCE CHARACTERISTICS:
          (A) LENGTH: 37 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:5:

Gly Ile Thr Cys Gly Met Val Ser Ser Lys Leu Ala Pro Cys Ile Gly
 1               5                  10                  15

Tyr Leu Lys Gly Gly Pro Leu Gly Gly Gly Cys Cys Gly Gly Ile Lys
                20                  25                  30

Ala Leu Asn Ala Ala
            35

(2) INFORMATION FOR SEQ ID NO:6:

(i) SEQUENCE CHARACTERISTICS:
          (A) LENGTH: 39 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:6:

Ala Ile Ser Cys Gly Gln Val Ser Ser Ala Ile Gly Pro Cys Leu Ala
 1               5                  10                  15

Tyr Ala Arg Gly Ala Gly Ala Ala Pro Ser Ala Ser Cys Gln Ser Gly
                20                  25                  30

Val Arg Ser Leu Asn Ala Ala
            35

(2) INFORMATION FOR SEQ ID NO:7:

(i) SEQUENCE CHARACTERISTICS:
          (A) LENGTH: 39 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:7:

Ala Ile Ser Cys Gly Gln Val Ala Ser Ala Ile Ala Pro Cys Ile Ser
 1               5                  10                  15

Tyr Ala Arg Gly Gln Gly Ser Gly Pro Ser Ala Gly Cys Cys Ser Gly
                20                  25                  30

Val Arg Ser Leu Asn Asn Ala
            35

-continued (2) INFORMATION FOR SEQ ID NO:8:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:8:

```
Ala Leu Asn Cys Gly Gln Val Asp Ser Lys Met Lys Pro Cys Leu Thr
1               5                   10                  15

Tyr Val Gln Gly Gly Pro Gly Pro Ser Gly Glu Cys Cys Asn Gly Val
                20                  25                  30

Arg Asp Leu His Asn Gln
                35
```

(2) INFORMATION FOR SEQ ID NO:9:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:9:

```
Ala Val Pro Cys Ser Thr Val Asp Met Lys Ala Ala Ala Cys Val Gly
1               5                   10                  15

Phe Ala Thr Gly Lys Asp Ser Lys Pro Ser Gln Ala Cys Cys Thr Gly
                20                  25                  30

Leu Gln Gln Leu Ala Gln
                35
```

METHOD FOR PROMOTING THE DIFFERENTIATION OF PLANT CELLS IN CULTURE

FIELD OF THE INVENTION

The present invention relates to a method for promoting the differentiation of cells in culture, in particular during the processes of tissue differentiation, embryogenesis or organogenesis. The invention relates, more specifically, to a method for obtaining embryos by culturing plant somatic cells and using lipid transfer proteins (LTPs) and to these proteins and their uses.

BACKGROUND OF THE INVENTION

The principle of obtaining embryos by culturing somatic cells in vitro is well known, on paper. In particular, see D. J. Gray and J. A. Mortensen, Plant Cell, Tissue and Organ Culture (1987) vol. 9 pp. 73–80. Regarding vine somatic embryos in particular, see U.S. Pat. No. 4,532,733. While somatic embryogenesis may be feasible for certain species of plants, this method is, by contrast, very difficult, if not impossible, to implement in the case of other species.

In order to understand the problems which are posed, it is necessary to recall briefly the principles of culturing somatic cells which are intended to form embryos.

Somatic embryogenesis essentially comprises two steps:
1—the induction of embryogenic potential using exogenous auxins, in general at high concentrations, which give rise to the appearance of proembryogenic aggregates (or masses) (PEM), which correspond to groups of from 10 to 50 cells which are, in particular, of a meristematic nature.
2—the transfer of these cells onto media which lack auxins and which lead to the formation of somatic embryos from these PEM, following the different developmental stages of plant embryogenesis, namely: globules, heart and torpedo.

In the case of certain plant species, it proves to be very difficult, if not impossible, to obtain somatic embryos. For example, in the case of certain vine cultivars, the embryogenic capacities of the somatic cells can either be halted, usually at the stage of proembryogenic aggregate formation, or else maturation of the embryos is blocked, in particular at the globular stage.

This is all the more unfortunate since there exists, in particular in the case of the vine, a very great need for obtaining somatic embryos, in vitro, on a large scale. Thus, the in vivo methods for producing embryos are often inadequate and undesirable since they lead, as a general rule, to genetic recombinations which involve the loss of the novel genetic features of the vine variety or the stock-vine whose multiplication is desired.

European patent application EP 281375 proposed adding calmodulin and calcium to a cell culture in order to promote differentiation of roots and embryos.

European patent application EP 455597 describes a method for stimulating the growth and embryogenesis of plants cultivated in vitro, by addition of arabino-galactan proteins. However, it has been demonstrated (de Vries et al., 1989, Proceedings of the International Symposium of Biotechnology for Major Crops (A.D.E.B.I.O. ed.), pages 22–23) that an extracellular glycoprotein of 52/54 kDa induces arrest in embryonic development at the heart stage.

SUMMARY OF THE INVENTION

The present invention is based on identifying proteins that ensure or stimulate cell differentiation, in particular somatic embryogenesis, even under certain nonpermissive conditions, in particular from vine somatic cells. It is also possible for the proteins to have other uses.

Within the meaning of the preceding paragraph, "nonpermissive conditions" are understood to mean, in relation to achieving a given phenomenon, conditions which are known from the state of the art partially or totally to prevent the phenomenon from being achieved.

This is why, in accordance with a first aspect, the present invention relates to a method for promoting the differentiation of cells in culture. In particular, the present invention relates to a method for promoting tissue differentiation, embryogenesis or organogenesis. The method is characterized in that at least one lipid transfer protein or "LTP", or one LTP analog, is introduced into the culture medium in a concentration which is effective for obtaining differentiation of the cells. An LTP analog is understood to mean any proteinaceous substance, such as a protein, protein fragment or polypeptide, which exhibits at least 30% homology with an LTP or an LTP fragment.

Preferably, the lipid transfer protein is an LTP obtainable from cells belonging to the same genus or the same species as the cells in culture.

According to a second aspect, the present invention relates to a method for obtaining plant somatic embryos from an in vitro culture of somatic cells. The method is characterized in that at least one lipid transfer protein, or LTP, or one LTP analog, is added to the culture medium in a concentration which is effective for ensuring embryogenesis.

According to a third aspect, the invention also relates to a plant which is obtained by any of the abovementioned methods of the invention.

According to a fourth aspect, the present invention relates to a proteinaceous substance having lipid transfer properties.

According to a fifth aspect, the present invention also relates to a DNA sequence which encodes a protein as defined in the previous aspect.

According to a sixth aspect, the present invention relates to uses of the proteinaceous substances of the invention.

Furthermore, the invention relates to a probe.

BRIEF DESCRIPTION OF THE DRAWINGS

FIG. 1 represents sequences of the P1, P2, P3 and P4 proteins;

FIG. 2 represents a comparison of the sequences of the LTPs from different species;

DETAILED DESCRIPTION OF THE INVENTION

Figure 3:
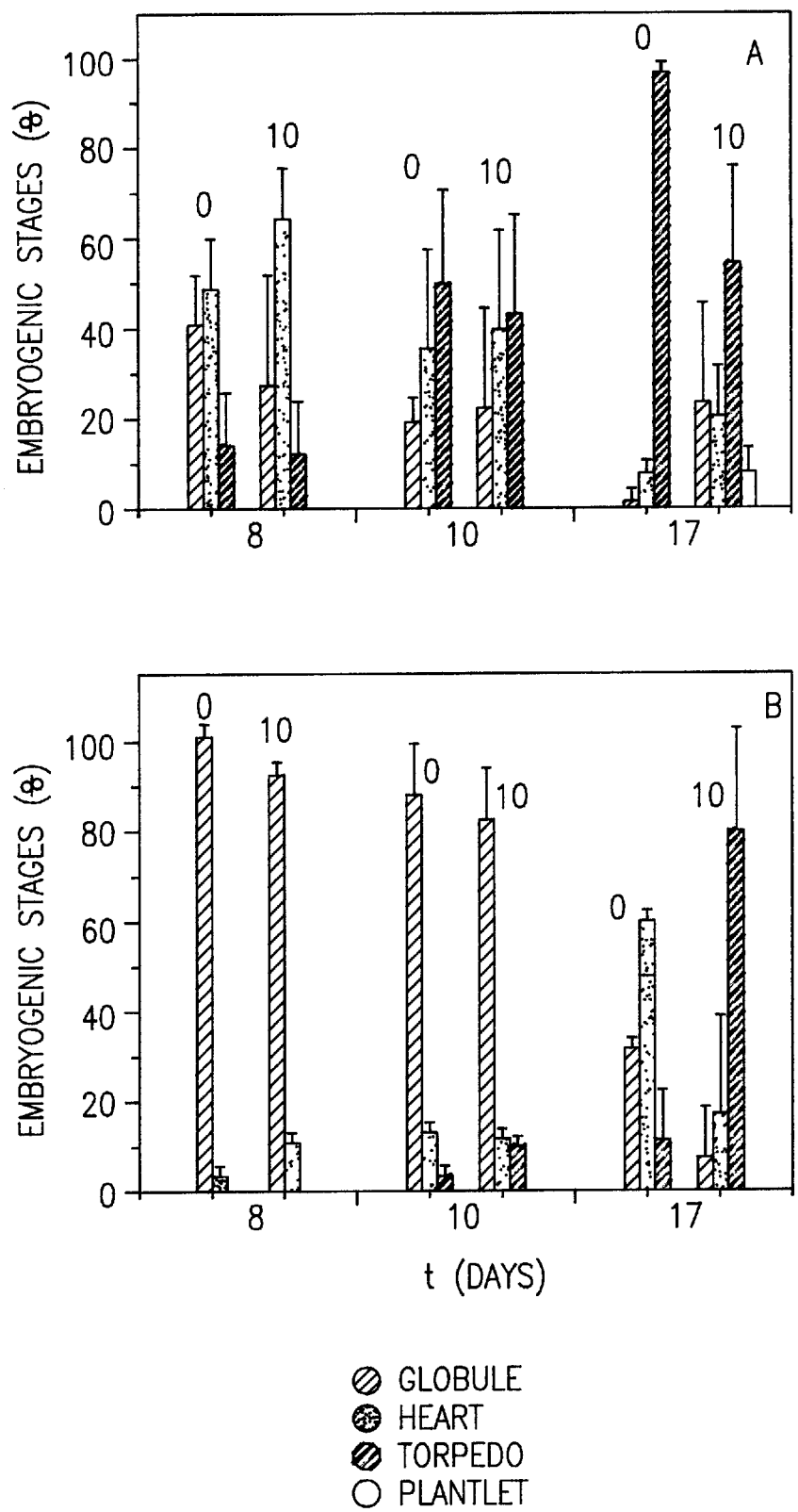
FIG. 3 represents the effect of adding the F1 fraction (P1, P2 and P3 proteins, Seq. ID's 1, 1, and 2) on embryo maturation in the presence of different concentrations of auxin and at two different cell densities, as compared with a control culture.

There are many reasons why somatic embryogenesis is blocked in the vine. In a general manner, the expression "nonpermissive conditions", as defined above, will be used to describe those conditions under which it is either impossible or at best very difficult to form embryos, or where embryo formation is very poor.

Similarly, in that which follows, the term maturation will be used in a general manner to designate the phenomena of development and germination of the somatic plant embryo, passing, as it were, through the following developmental stages: globule, heart, torpedo and plantlet.

The technology for cell culture of somatic cells in vitro is known and has, of course, to be adapted to each of the cells involved. The physicochemical conditions, the culture media and the environment are adapted to allow multiplication and formation of proembryogenic aggregates, and then embryogenesis. The corresponding media will be termed "culture media for embryogenesis".

The LTPs which may be employed in accordance with the invention can be introduced at any time into the culture medium. Thus, it was demonstrated that, when the somatic cells were placed under conditions which were not permissive for embryogenesis, it was possible, nevertheless, to observe the formation of embryos when lipid transfer proteins were added to the culture medium.

Kader et al. (Methods Enzymol., 1987, 148, 661–666) have identified an LTP which is isolated from young corn plants. Nonspecific lipid transfer proteins have been characterized in castor oil feed endosperm, spinach leaves and barley aleurone. LTPs are also present in carrot and in millet. The LTPs known from the plant kingdom are proteins which generally have a molecular weight of about 10 kDa; the nonspecific LTPs and the majority of the specific LTPs are basic proteins which have an isoelectric point which is greater than 8.

The inventors were able to demonstrate that the presence of auxin in the medium, which frequently results in the appearance of nonpermissive conditions, was not an obstacle to embryo formation if LTPs were added.

According to one embodiment of the method, the LTP or LTP analog is added to the medium for inducing and/or for multiplying the aggregates of proembryogenic cells, which medium generally contains an auxin. An increase in the embryogenic capacity of the strain is then observed, as is an increase in the number of proembryogenic aggregates formed.

The method according to the present invention is also particularly advantageous for achieving the formation of embryos, and their maturation, especially when the cells are transformed cells. Thus, in accordance with the invention, the LTPs can be introduced into the embryo maturation medium which is, in accordance with prior art, generally free of auxin, or more or less free of auxin. However, it is an advantage of the invention that, even in the presence of auxin, and despite this presence, addition of LTP promotes or permits maturation of the embryos.

Thus, in accordance with a particular embodiment of the invention, the LTP or LTP analog is added to the embryo maturation medium. This maturation medium can be more or less free of auxin. However, in accordance with another variant of the method for obtaining plant somatic embryos, the maturation medium contains one auxin, in particular in a quantity which is necessary for ensuring the viability of the cell culture.

Auxins which may be cited are 2,4-dichlorophenoxyacetic acid (2,4 D), 1-naphthaleneacetic acid (NAA) and 2-naphthoxyacetic acid (NOA).

In particular, it can be advantageous to use LTPs in media for culturing transformed cells, in particular vine cells, especially when the cell strain exhibits disturbed somatic embryogenesis. For example, when these cells have been transformed biolistically (by means of a particle gun) or with suitable cloning vectors such as vectors derived from Agrobacterium, or other systems of a viral type. In this case, there is no absolute requirement for the multiplication step to take place, and maturation can take place directly.

According to a particular embodiment of the method according to one or other of the two previously mentioned aspects, the LTP or LTP analog is present in the culture medium at a concentration of between 1 and 100 µg/ml of medium, preferably between 1 and 50 µg/ml.

According to another particular embodiment in accordance with one or other of these two aspects, the abovementioned culture of cells is a culture of vine cells.

According to other, different, embodiments of the method in accordance with one or other of the two abovementioned aspects, the LTP or LTP analog encompasses at least one amino acid sequence which exhibits at least 80% homology with one of the sequences depicted in FIG. 2 (Seq. ID's 1–9).

In particular, the abovementioned LTP or LTP analog encompasses at least one amino acid sequence which exhibits virtually 100% homology with one of the sequences depicted in FIG. 2 (Seq. ID's 1–9).

The LTP or LTP analog also has a molecular weight of approximately 9 kDa.

Preferably, the lipid transfer protein is an LTP which can be obtained from cells belonging to the same genus or the same species as the cells in culture. For example, in the case of vine embryogenesis, it is advantageous to employ, as will be described in more detail below, P1, P2, P3 or P4 proteins corresponding to Seq. ID's 1, 2, and 3, respectively, of vine, as well as their derivatives, with the polypeptides and their fragments preferably having lipid transfer properties.

In particular, it is possible to employ an LTP from vine, carrot, spinach, millet, maize, barley or rape.

According to a third aspect, the invention also relates to a plant which is obtained by any of the abovementioned methods of the invention.

Among the LTPs which can be employed, in particular in the case of vine embryos, it is necessary to mention, more particularly, four proteins which have been identified within the scope of the present invention. The proteins include P1, P2, P3 and P4, corresponding to Seq. ID's 1, 1, 2, and 3, respectively, as well as the proteins or fragments of the proteins or polypeptides which exhibit at least 80% homology with at least one of these proteins, or the corresponding fragments of the proteins. In particular, the proteins, polypeptides and fragments include proteins which are partially deleted but which have preferably retained their lipid transfer capacities.

The N-terminal sequences of these four proteins (Seq. ID's 1–3) are indicated in the attached FIG. 1. The purity of these proteins was confirmed by the presence of a single type of N-terminal end for each sample. The corresponding proteins are proteins which are not N-glycosylated.

Thus, in accordance with a fourth aspect, the present invention relates to a proteinaceous substance which consists, in particular, of a protein, of a protein fragment or of a polypeptide. The proteinaceous substance encompasses an amino acid sequence, which is preferably situated at its N-terminal end, which exhibits at least 80% homology with one of the sequences (Seq. ID's 1–3) depicted in FIG. 1, and which preferably possesses an activity for transferring lipids, in particular phospholipids.

In particular, the proteinaceous substance encompasses an amino acid sequence which exhibits virtually 100% homology with one of the sequences (Seq. ID's 1–3 depicted in FIG. 1.

The P1, P2, P3 and P4 proteins, corresponding to Seq. ID's 1, 1, 2, and 3, respectively, which will be described in more detail below, conform to the previous definition.

While the P1 and P2 proteins exhibit the same sequence for the first 40 amino acids (Seq. ID 1) counting from the N-terminal end, the amino acid compositions of P3 and P4 proteins are different (Seq. ID's 2 and 3). It follows from this observation that the P1 and P2 proteins, both corresponding to Seq. ID 1, having the same sequence, could represent one and the same protein, which was subjected to post-translational modifications. On the other hand, P3 and P4, Seq. ID's 3 and 4, respectively, two other isoforms. The sequences of these proteins also exhibit a great deal of similarity with other protein sequences which have been established for other plant species.

The homologies between the sequences of the first 40 amino acids, counting from the N-terminal end, of LTPs of different origin were analyzed using the University of Wisconsin Genetic Computer Group software (Nucleic Acid Research. 12, 387–395, 1984). This analysis is represented in FIG. 2 (Seq. ID's 1–9).

The numbering of the amino acids is fixed in terms of the system employed for determining the homologies between the different LTPs, as shown in FIG. 2 (Seq. ID's 1–9). This numbering takes into account the gap which is necessary in order to obtain the alignments for maximum homology.

It is observed that, in these proteins, the positions of certain amino acids are conserved, as follows:

2 cysteines, at positions 4 and 14, respectively, 1 or 2 cysteines, at positions 30 and 31, respectively, 1 valine, at position 7, 1 tyrosine, at position 17, 1 leucine, at position 37, and, with a very strong degree of probability, 3 glycines, in positions 5, 22 and 33, respectively, 1 proline in position 25, 1 lysine in position 35, 1 alanine in position 40.

The molecular weights of the P1, P2, P3 and P4 vine proteins, corresponding to Seq. ID's 1, 1, 2, and 3, respectively, are given in Table I:

TABLE I

| Proteins | Mean calculated weight (Da) |
|---|---|
| P1 (Seq. ID 1) | 9102.5 ± 3.0 |
| P2 (Seq. ID 1) | 9270.5 ± 0.4 |
| P3 (Seq. ID 2) | 9273.0 ± 3.1 |
| P4 (Seq. ID 3) | 9090.2 ± 7.0 |

The four proteins, Seq. ID's 1–3 in question possess lipid transfer activity. This activity was demonstrated by measuring the in vitro transfer of tritiated phosphatidylcholine between liposomes (donor membrane system), which consists of this phospholipid, and mitochondria, constituting the recipient membrane system, in accordance with the method described by Douady D. et al. in Biochim. Biophys. Acta (1982) vol. 710 pp. 143–153.

However, the specific activities of these proteins, Seq. ID's 1–3 are rather different, as indicated in Table II.

TABLE II

| Proteins | Specific activity (nmol · min$^{-1}$ · mg$^{-1}$ prot) |
|---|---|
| P1 (Seq. ID 1) | 15 |
| P2 (Seq. ID 1) | 17.8 |
| P3 (Seq. ID 2) | 4.3 |
| P4 (Seq. ID 3) | 5.3 |
| Purified corn LTP | 5.7 |

It is noted that while the P1 and P2 proteins, both corresponding to Seq. ID 1, exhibit very high specific activity, the activity of the P3 and P4 proteins, Seq. ID's 3 and 4 is three times lower.

While a method will be given in the examples which allows these proteins to be isolated by means of physico-chemical methods, it is, of course, understood that, knowing the sequence of the first forty amino acids, it is possible to deduce from this a DNA sequence which encodes the proteins and, therefore, to synthesize these proteins using recombinant cells.

Thus, according to a fifth aspect, the present invention also relates to a DNA sequence which encodes a protein as defined in the previous aspect.

According to a sixth aspect, the present invention also relates to the different uses of proteinaceous substances, as previously defined, within the description of the fourth aspect of the invention. In particular, the uses are in compositions which contain the proteinaceous substances either alone or in association with other active principles, in particular lipid compounds. While these compositions may be used, for example, as additives for cell cultures, they can also be used for other applications within the biological sphere in which their lipid transfer activity and/or their effect on tissue differentiation proves to be invaluable.

Lastly, according to a final aspect, the present invention also relates to a probe which consists of at least one oligonucleotide. The probe is characterized in that the base sequence of the oligonucleotide is deduced from a part of the amino acid sequence of a proteinaceous substance such as previously defined, in particular of one of the proteins P1 to P4 , Seq. ID's 1–3. These probes, which are labeled using methods known to the person skilled in the art (Molecular cloning, A. Laboratory Manual, T. Maniatis, E. F. FRITSCH, J. SAMBROOK, Cold Spring Harbour [sic] Laboratory 1982) will be employed for detecting endogenous LTPs and for making an objective assessment of the processes of cellular differentiation.

More particularly, the abovementioned oligonucleotide sequence is deduced from an amino acid sequence which comprises at least 6 or 7 amino acids, preferably counting from position 3 of the N-terminal end of the proteinaceous substance, in particular the protein.

The probe can also consist of a mixture of oligonucleotides such as previously defined.

The examples below are intended to illustrate other features and advantages of the present invention.

EXAMPLE 1

Preparation of the P1, P2, P3 and P4 (Seq. ID's 1–3)

A suspension of vine cells derived from the line 41 B (*Vitis vinifera* cv. Chasselas×*Vitis berlandieri*) is employed. Undifferentiated growth of these cells is maintained by carrying out weekly subcultures in the presence of auxin, 2-naphthoxyacetic acid (NOA), at a concentration of 5 μM, as previously described by Coutos-Thevenot et al. in Plant Cell Tissue Organ Culture 29, 125–133 (1992).

In order to initiate embryogenic differentiation, the filtered cells are washed in an auxin-free medium and inoculated, in an amount of 1 μl, into a GMo culture medium in accordance with the protocol described in the same publication.

After 15 days of incubation, the medium is harvested by first of all separating off the PEMs or the embryos using a No. 2 and No. 4 glass particle filter (Pyrex, France), respectively. The conditioned medium is clarified by passing it, in vacuo, through a glass fiber membrane (Whatman GF/C), and concentrated from 100 to 200 times using an AMICON ultrafiltration system with a YM3 AMICON membrane (cut-off threshold, 3 kDa). The protein content is determined by the Lowry method.

The proteins are purified with the aid of an HPLC system (Waters, Mass., USA) employing a UV M 440 detector under the following conditions:

1) the medium, which has been harvested after 15 days of incubation and concentrated 100 times, is loaded onto a cation exchange column (type SP5PW from Waters, Mass., USA) which has previously been equilibrated with a 25 mM sodium phosphate buffer, pH 6.5 (flow-rate 0.8 ml/minute). Approximately 4 mg of proteins are placed on the column. The basic proteins are eluted within 30 minutes using a linear gradient of aqueous solutions of sodium chloride of from 0 to 0.3 M. The fractions corresponding to the different peaks observed on the elution profile are collected and analyzed by SDS PAGE electrophoresis. Two fractions having a molecular weight of approximately 10 kDa are obtained, and these fractions are subsequently subjected to a second purification step. The F1 fraction represents 15.3% by weight of the initial basic proteins while the F2 fraction represents 10.2%

2) The samples, which are diluted 1 to 1 by volume with a buffer (3.6 M ammonium sulfate, 100 mM sodium phosphate, pH 7), are loaded onto a hydrophobic column (HIC PH214 from Shodex, Tokyo, Japan) whose mobile phase is a buffer solution at pH 7 which contains 1.8 moles [sic] of ammonium sulfate and 100 mM sodium phosphate. The flow-through rate is 1 ml/min. The bound proteins are eluted within 30 min using a descending linear gradient of from 1.8 M to 0 M ammonium sulfate. The fractions corresponding to the different peaks are collected and desalted on Sephadex G25M (PD-10 from Pharmacia). After determining the protein concentrations by the Lowry method, the fractions are concentrated using a Speedvac concentrator (SPD2DVAC model, SVC 100H model from Savant Instrument Inc. New York, USA).

The elution profile obtained for the first major peak (F1 fraction) of step 1 provides 3 secondary peaks corresponding to the P1, P2 and P3 proteins, corresponding to Seq. ID's 1, 1, and 2, respectively. The P4 protein, Seq. ID 3, is recovered in the eluate from the second major peak (F2 fraction) of step 1.

After this chromatographic treatment, 42.5 μg of P1 Seq. ID 1), 6.54 μg of P2 (Seq. ID 1) and 0.33 μg of P3 (Seq. ID 2) are recovered from 100 μg of the F1 fraction. 46 μg of P4 (Seq. ID 3) are recovered from 100 μg of the F2 fraction.

EXAMPLE 2

Analysis of the P1, P2, P3 and P4 Proteins (Seq. ID's 1–3)

a) Determination of the molecular weights

The molecular weights of the P1, P2, P3 and P4 proteins, corresponding to Seq. ID's 1, 1, 2, and 3, respectively, were determined in a conventional manner by means of mass spectrometry. The results are given in Table I.

b) Determination of the amino acid sequences

The N-terminal sequence of 40 amino acids was analyzed using a gas-liquid phase 470A sequencer (ABI, Foster City, Calif.). The phenylhydantoin amino acids are analyzed on a 120A on-line analyzer.

The results of this analysis are depicted in the attached FIG. 1 (Seq. ID's 1–3).

The sequences of P1 to P4 (Seq. ID's 1–3) were compared with the sequences of LTP proteins from carrot (c) (Seq. ID 4), spinach (s) (Seq. ID 5), millet (Mi) (Seq. ID 6), and from corn (M) (Seq. ID 7).

The percentage homologies between these proteins for the first 40 amino acids are given in Table III.

TABLE III

| LTP | P1 | P2 | P3 | P4 | C | S | Mi | M |
|---|---|---|---|---|---|---|---|---|
| P1 | 100 | 100 | 32 | 53 | 35 | 63 | 45 | 37 |
| P2 |  | 100 | 32 | 53 | 35 | 63 | 45 | 37 |
| P3 |  |  | 100 | 32 | 35 | 43 | 35 | 43 |
| P4 |  |  |  | 100 | 36 | 39 | 38 | 41 |
| C |  |  |  |  | 100 | 32 | 36 | 44 |
| S |  |  |  |  |  | 100 | 37 | 39 |
| Mi |  |  |  |  |  |  | 100 | 74 |
| M |  |  |  |  |  |  |  | 100 |

It is noted that while there is total homology between the P1 and P2 proteins (Seq. ID 1), the homology between the P3 and P4 proteins (Seq. ID's 2 and 3) is lower.

c) Determination of lipid transfer activity

The four protein fractions, and an LTP purified from corn, employed as control, are tested for their lipid transfer activity using the technique described by Douady, D., Grosbois, M., Guerbette, F. and Kader, J. C. (1982) Biochim. Biophys. Acta 710, 143–153. The proteins are incubated at 30° C. for 30 minutes with purified corn mitochondria and with a preparation of radioactive liposomes. The labeling is carried out with, on the one hand, tritiated phosphatidylcholine, and, on the other hand, with a lipid which cannot be transferred by these LTPs: cholesteryl (1–14C)-oleate. After centrifugation, the mitochondria are resuspended in 1% Triton X 100, and the ratio of the 3H and 14C activities (in cpm) is measured in order to determine the transfer activity, which is expressed as the percentage of tritiated phosphatidylcholine which is transferred after correction for the contaminating radioactivity caused by unexchanged cholesteryl oleate.

The proteins can be classified into two groups in terms of their ability to transfer phospholipids (cf. Table II). The P1 and P2 proteins (Seq. ID 1) exhibit high specific activities while the activities of the P3 and P4 proteins, Seq. ID's 1–3, are three times lower and close to those found for corn LTP.

EXAMPLE 3

Effect of the P1, P2 and P3 Proteins (Seq. ID's 1–3) on the Initiation and Maturation of Embryos 1) Material and methods The culture medium which is employed for developing somatic embryos is a modified MS liquid culture medium which includes, in particular 18 g/l maltose and 4.6 g/l glycerol in place of sucrose and 1 g/l casein hydrolyzate.

This medium is employed at a pH which is adjusted to 5.8 using 0.1 N sodium hydroxide solution; the medium is then used as it is or else following the addition of NOA (naphthoxyacetic acid) at concentrations of 0.5 $\mu$M or 5 $\mu$M.

The culture medium is autoclaved at 120° C. for 20 min. The undifferentiated cell cultures, derived from the cell culture maintained in accordance with the protocol described in Example 1, are filtered successively through nylon filters having a pore size of 500 $\mu$m and then 200 $\mu$m so that only cell aggregates having a size between these two values are retained for the culture inoculation.

The undifferentiated cell aggregates retained on the second filter are then washed 3 times with the modified MS medium, after which they are suspended in 30 ml of this medium.

The cell density, expressed in $\mu$l of cell volume per ml of medium, is determined after sedimenting (1×g) the cells in a conical graduated tube.

A 250 ml Erlenmeyer flask is then inoculated with 80 ml of modified MS culture medium containing a suspension of cell aggregates at a density of 0.1 or 1 $\mu$l/ml and, as the case may be, either no NOA or NOA at a concentration of 0.5 or 5 $\mu$M.

While, for experimental applications, the volumes of culture medium can be reduced to approximately 1 ml in 24-well microtitration plates (Falcon), the cell density must be respected.

The culture media are then supplemented, at To of the experiment, with increasing doses of the F1 protein fraction, which is isolated as described in Example 1 and essentially contains the P1, P2 and P3 LTPs. The respective doses are 2 and 10 $\mu$g/ml; a control lacking LTP is also cultured.

2) Effects on initiation

Figure 4:
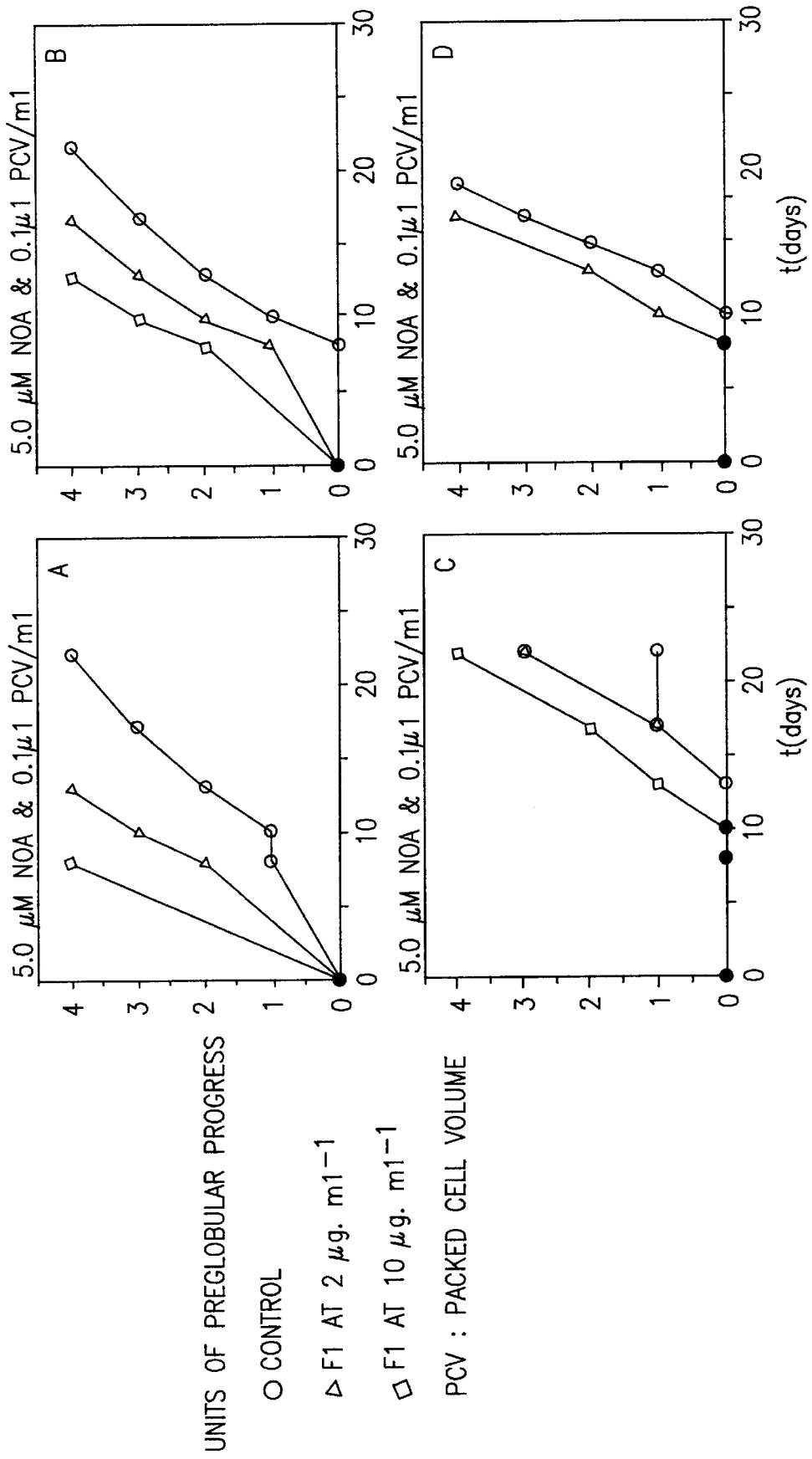
FIG. 4 represents the effect of adding the F1 fraction on differentiation in the preglobular stage, in the presence of different concentrations of auxin and at two different cell densities.

FIG. 4 depicts the development of the proembryogenic aggregates towards the first globular stage of the embryo, in the presence of auxin concentrations of, respectively, 0.5 and 5 $\mu$M, for densities of the cell aggregates of 0.1 and 1 $\mu$l/ml which are expressed in unit of packed cell volume (PCV) per unit volume of medium.

The proembryogenic structure development curves are drawn using arbitrary units: 0 for undifferentiated PEMs, 4 for embryos at the globular stage, and values of 1, 2 and 3 corresponding to intermediate stages of proglobular embryos in the cellular mass.

With 0.5 $\mu$M NOA and an aggregate density of 0.1 $\mu$l/ml, without LTP being added, the first globules only appear after 21 days.

This delay in appearance of the first globules is shortened to 11 days when the medium is supplemented with 2 $\mu$g/ml LTP, and to 6 days when the medium is supplemented with 10 $\mu$g/ml LTP. The same effect is observed for a density of 1 $\mu$l/ml, with a slight delay.

There is, therefore, a very substantial acceleration in embryo development when the medium contains an LTP.

When 5 $\mu$M NOA is present, globules are not formed in the cultures unless the latter have been supplemented with LTPs.

When an initial cell density of 0.1 $\mu$l/ml is used, perfectly differentiated globules are obtained at 21 days in medium supplemented with 10 $\mu$g/ml F1 fraction.

When the initial cell density is 1 $\mu$l/ml, the auxin is metabolized rapidly and differentiation begins even in the absence of LTP. The differentiation is accelerated by supplementing with F1 fraction.

3) Results on the maturation of embryos

In the absence of auxin, the total time taken for the embryos to develop, passing through the different globular, heart and torpedo stages of development, is approximately 15 days when 10 $\mu$g/ml LTP are present.

FIG. 3 shows the progress of embryogenesis by counting the proportions of embryos at the different stages in their development, in a medium which does not contain auxin, in relation to the total number of embryos. The culture medium is supplemented, at the beginning of the culture period, either with F1 fraction at a protein concentration of 10 $\mu$g/ml (10) or with an equivalent volume of buffer (0). The results obtained for an initial cell density of 0.1 $\mu$l/ml are depicted in A; those for an initial density of 1 $\mu$l/ml are depicted in B.

(A) at 0.1 $\mu$l PCV/ml.

At this cell density, the embryos are not blocked under standard culture conditions and can reach the plantlet stage.

While plantlets have already appeared at 17 days when LTP is present, the embryos in the control are still at the torpedo stage at this time.

There is, therefore, an acceleration in the development of the embryos.

(B) at 1 $\mu$l of PCV/ml.

Under these density conditions, the embryos are generally blocked at the heart stage.

At 17 days, the majority of the embryos are at the heart stage, and remain blocked at this stage, when LTP is absent.

When LTP is present, the majority of the embryos are at the torpedo stage: there is, therefore, an acceleration in the development of the embryos without any blockage being produced at a specific stage.

Moreover, it has been demonstrated that, in the presence of auxin and in the absence of LTP, development of the embryos is blocked at the globule stage. By contrast, as a result of adding LTP to the culture medium, no blockage is observed. For example, adding 10 $\mu$g/ml of F1 fraction at time To to the culture medium containing the auxin NOA at a concentration of 0.5 $\mu$M makes it possible, after 21 days of culture, to obtain, per 100 counted embryos: 59 at the globule stage, 20 at the heart stage, 11 at the torpedo stage and 9 at the plantlet stage.

EXAMPLE 4

Effect of the P4 Protein (Seq. ID 3) on Embryo Maturation

The medium is supplemented, in accordance with a protocol which is similar to that described in Example 3, with the F2 fraction, which essentially contains the P4 LTP.

Figure 5:
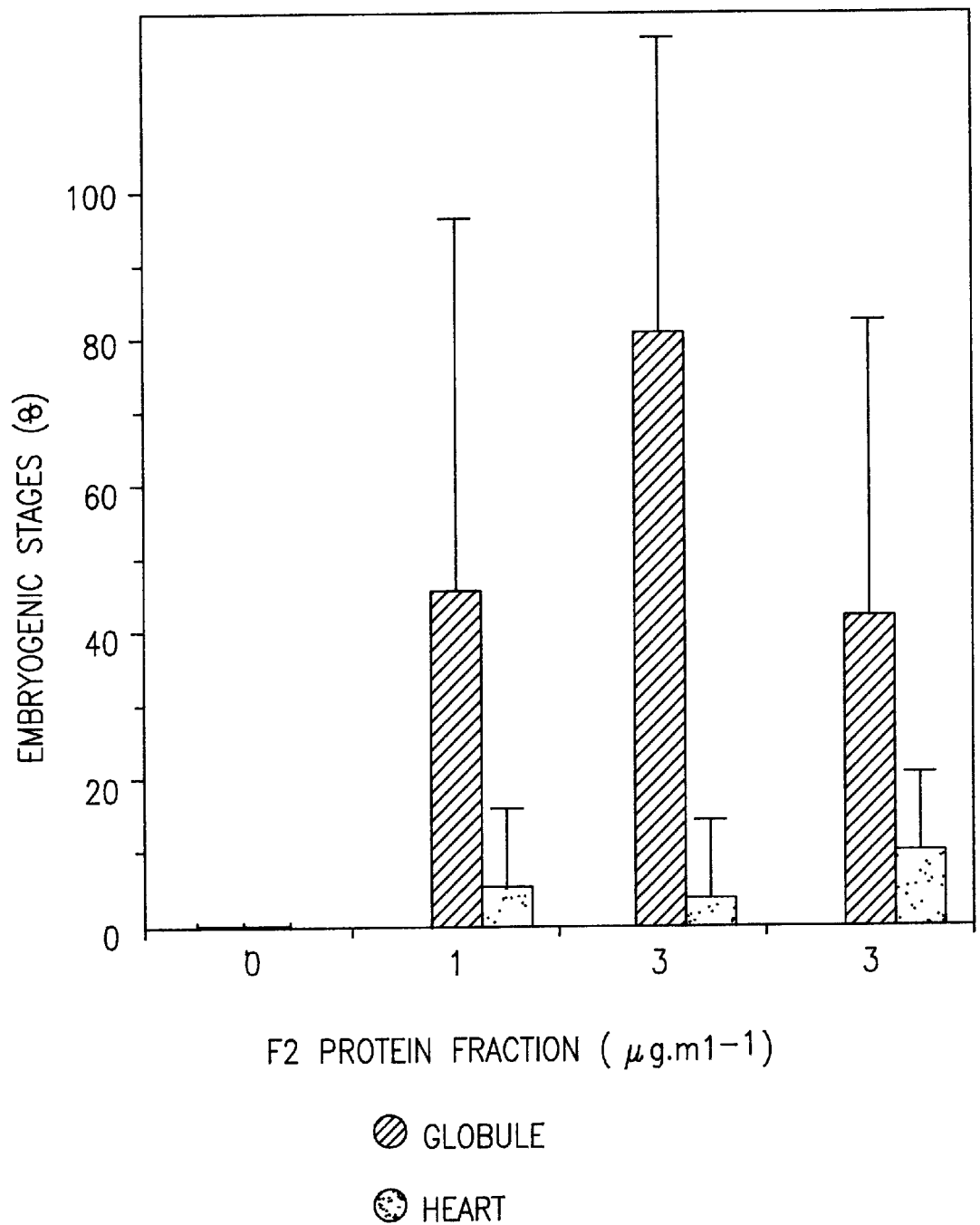
FIG. 5 represents the effect of adding different concentrations of the F2 fraction (P4 protein, Seq. ID 3) on embryo maturation.

FIG. 5 shows the results which are obtained, after 21 days of culture and in the presence of NOA at a concentration of 5 $\mu$M, for an initial cell density of 0.1 $\mu$l/ml and in the presence of different concentrations of the F2 fraction: 0, 1, 2 and 3 $\mu$g/ml.

There is no differentiation in the absence of LTP. Differentiation is induced by supplementing the medium with F2 fraction.

The effect of the F2 fraction takes more time to appear. At 21 days of culture, only a small proportion of embryos have reached the heart stage.

We claim:

1. A method for promoting differentiation of cells in culture, said method comprising the steps of:
   introducing at least one lipid transfer protein into a culture medium at a concentration that is effective for obtaining differentiation of cells in the culture medium, said lipid transfer protein including at least one amino acid sequence having at least 80% homology with Seq. ID No. 1, Seq. ID No. 2, or Seq. ID No. 3.

2. A method according to claim 1, wherein said lipid transfer protein or lipid transfer protein analog is present in the culture medium at a concentration of from 1 µg/ml to 50 µg/ml.

3. A method according to claim 1, wherein the cells in the culture medium are vine cells.

4. A method according to claim 1, wherein said lipid transfer protein or lipid transfer protein analog has a molecular weight of about 9 kDa.

5. A method according to claim 1, wherein said lipid transfer protein is a lipid transfer protein obtainable from cells belonging to the same genus as the cells in the culture medium.

6. A method according to claim 1, wherein said lipid transfer protein is from a vine, carrot, spinach, millet, corn, barley, or rape.

7. The method for promoting differentiation of cells in culture according to claim 1, wherein said lipid transfer protein promotes at least one type of cell differentiation selected from the group consisting of tissue differentiation, embryogenesis, and organogenesis.

8. The method for promoting differentiation of cells in culture according to claim 1, wherein said homology is in the vicinity of the N-terminal end of said lipid transfer protein or lipid transfer protein analog.

9. A method for obtaining plant somatic embryos from an in vitro culture of somatic cells according to of claim 8, wherein said lipid transfer protein or lipid transfer protein analog is added to the culture medium for promoting embryo maturation.

10. A method according to claim 9, wherein said lipid transfer protein or lipid transfer protein analog included at least one amino acid sequence having substantially 100% homology with Seq. ID No. 1, Seq. ID No. 2, or Seq. ID No. 3.

11. A method according to claim 10, wherein said lipid transfer protein or lipid transfer protein analog has a molecular weight of about 9 kDa.

12. A method for obtaining plant somatic embryos from an in vitro culture of somatic cells according to claim 9, wherein said culture medium is substantially free of auxins.

13. A method for obtaining plant somatic embryos from an in vitro culture of somatic cells according to claim 9, wherein said culture medium includes an auxin.

14. A method for obtaining plant somatic embryos from an in vitro culture of somatic cells according to claim 9, wherein said culture medium includes an auxin at a concentration sufficient to ensure viability of the culture.

15. A method according to claim 9, wherein said lipid transfer protein or lipid transfer protein analog is present in the culture medium at a concentration of from 1 μg/ml to 100 μg/ml.

16. A method according to claim 9, wherein said lipid transfer protein or lipid transfer protein analog is present in the culture medium at a concentration of from 1 μg/ml to 50 μg/ml.

17. A method according to claim 9, wherein the cells in the culture medium are vine cells.

18. A method for obtaining plant somatic embryos from an in vitro culture of somatic cells, said method comprising the steps of:

introducing at least one lipid transfer protein into the culture medium at a concentration that is effective for initiating embryogenesis, said lipid transfer protein including at least one amino acid sequence having at least 80% homology with Seq. ID No. 1, Seq. ID No. 2, or Seq. ID No. 3.

19. The method for obtaining plant somatic embryos from an in vitro culture of somatic cells according to claim 18, wherein said homology is in the vicinity of the N-terminal end of said lipid transfer protein or lipid transfer protein analog.

20. A method for obtaining plant somatic embryos from an in vitro culture of somatic cells according to claim 18, wherein said lipid transfer protein or lipid transfer protein analog is added to the medium for inducing aggregates of proembryogenic cells, and wherein said culture medium includes an auxin.

21. A method for obtaining plant somatic embryos from an in vitro culture of somatic cells according to claim 18, wherein said lipid transfer protein or lipid transfer protein analog is added to the medium for multiplying aggregates of proembryogenic cells, and wherein said culture medium includes an auxin.

22. A method according to claim 18, wherein said lipid transfer protein or lipid transfer protein analog is present in the culture medium at a concentration of from 1 μg/ml to 50 μg/ml.

23. A method according to claim 18, wherein the cells in the culture medium are vine cells.

24. A method according to claim 18, wherein said lipid transfer protein or lipid transfer protein analog included at least one amino acid sequence having substantially 100% homology with Seq. ID No. 1, Seq. ID No. 2, or Seq. ID No. 3.

25. A method according to claim 18, wherein said lipid transfer protein or lipid transfer protein analog has a molecular weight of about 9 kDa.

26. A method according to claim 18, wherein said lipid transfer protein is a lipid transfer protein obtainable from cells belonging to the same genus as the cells in the culture medium.

27. A method according to claim 18, wherein said lipid transfer protein is from a vine, carrot, spinach, millet, corn, barley, or rape.

28. A method according to any one of claims 1, 7, 8, 12, 13, 14, 18, 19, 20 or 21, wherein said lipid transfer protein or lipid transfer protein analog is present in the culture medium at a concentration of from 1 μg/ml to 100 μg/ml.

29. A method according to any one of claims 1, 7, 8, 18, 19, 20, 21, 12, 13 or 14, wherein said lipid transfer protein or lipid transfer protein analog included at least one amino acid sequence having substantially 100% homology with Seq. ID No. 1, Seq. ID No. 2, or Seq. ID No. 3.

* * * * *